United States Patent [19]
Schaar

[11] 3,943,930
[45] Mar. 16, 1976

[54] DISPOSABLE DIAPER

[75] Inventor: Charles H. Schaar, Lake Zurich, Ill.

[73] Assignee: Colgate-Palmolive Company, New York, N.Y.

[22] Filed: Oct. 3, 1974

[21] Appl. No.: 511,848

[52] U.S. Cl. .............................................. 128/287
[51] Int. Cl.² ......................................... A61F 13/16
[58] Field of Search ..................... 128/287, 286, 284

[56] References Cited
UNITED STATES PATENTS

| | | | |
|---|---|---|---|
| 318,141 | 5/1885 | Samuel | 128/287 |
| 3,030,956 | 4/1962 | Nichols | 128/284 |
| 3,592,194 | 7/1971 | Duncan | 128/287 |
| 3,719,189 | 3/1973 | Sherman | 128/287 |
| 3,747,601 | 7/1973 | May, Jr. | 128/284 |
| 3,816,227 | 6/1974 | Schaar | 128/287 X |
| 3,848,599 | 11/1974 | Schaar | 128/287 |

*Primary Examiner*—John D. Yasko
*Attorney, Agent, or Firm*—Powell L. Sprunger

[57] ABSTRACT

A disposable diaper comprising, an absorbent pad assembly having a pair of waistline portions, a crotch region intermediate the waistline portions, a fluid impervious backing sheet, a fluid pervious cover sheet, and an absorbent pad intermediate the backing and cover sheets. The pad assembly may have a plurality of longitudinally extending folds defining a pleated configuration of the pad assembly having a longitudinally extending central panel, and a pair of outermost panels overlying the central panel. The pad assembly also has a lateral fold of the pleated pad assembly in the crotch region. The diaper has means for securing a sufficient portion of the outermost panels together in the lateral fold to maintain the pad assembly in its laterally folded configuration, in order that the diaper assumes a contoured configuration responsive to longitudinal expansion of the central panel.

23 Claims, 8 Drawing Figures

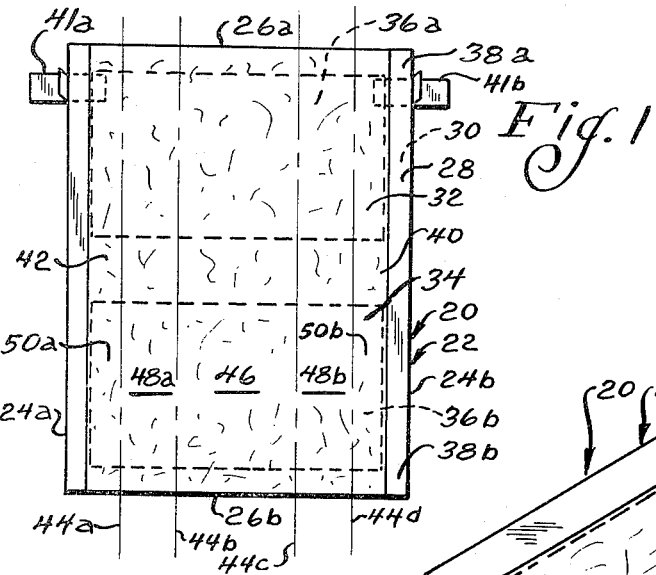
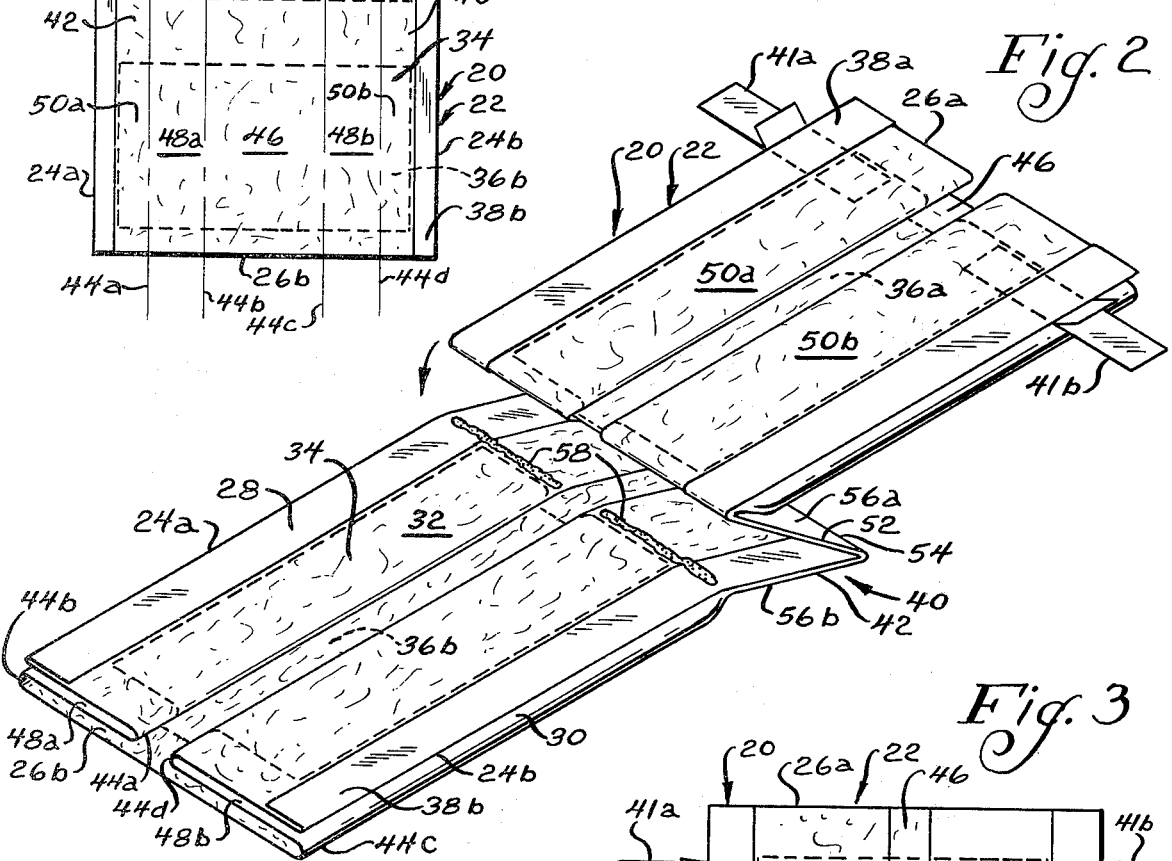
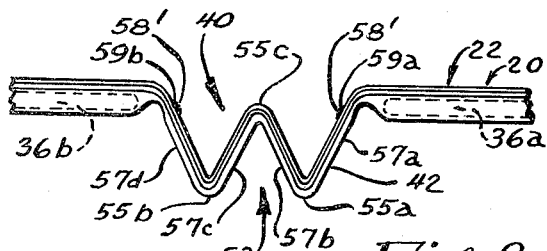
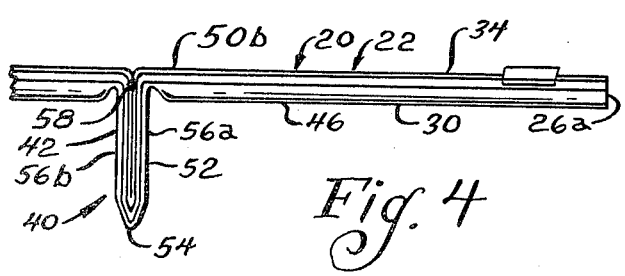
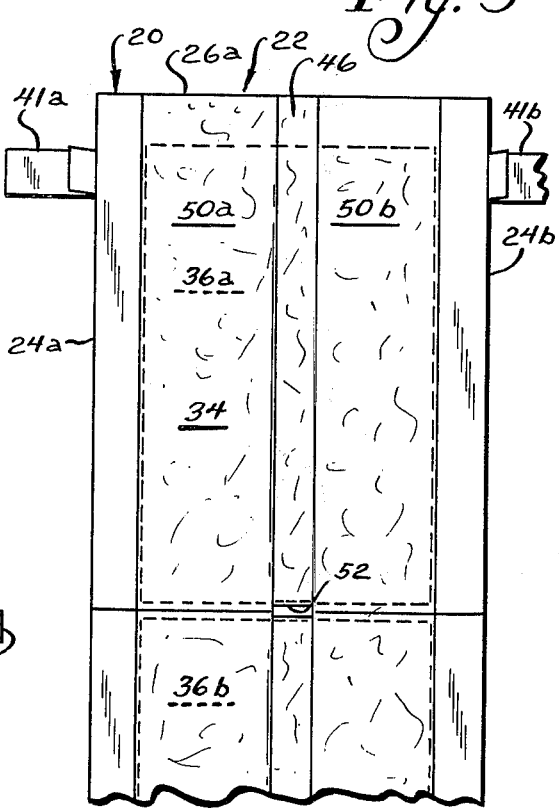

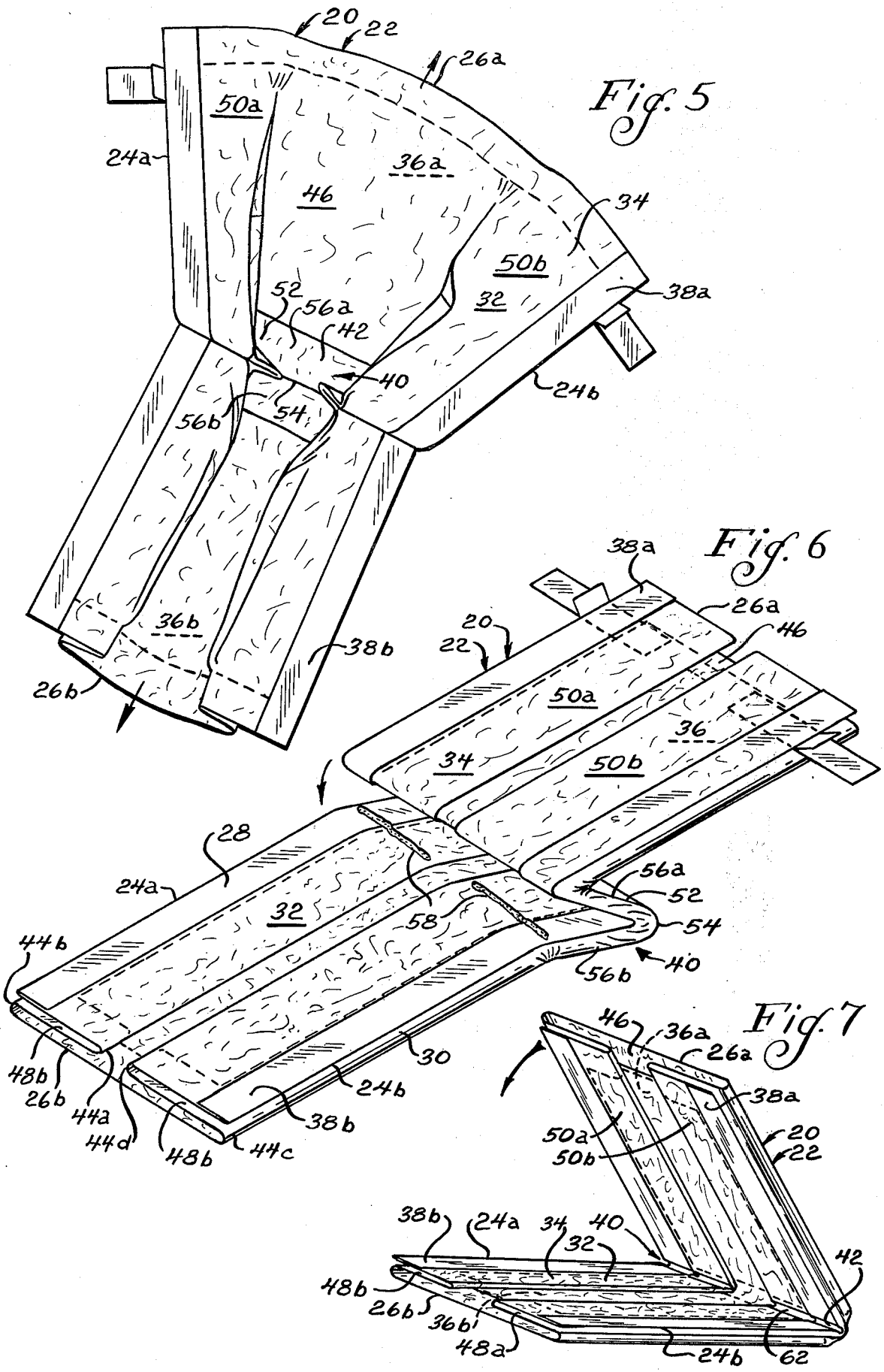

DISPOSABLE DIAPER

BACKGROUND OF THE INVENTION

The present invention relates to absorbent articles, and more particularly to disposable diapers.

A various assortment of disposable diapers have been proposed for use on infants. Although some of these diapers have achieved popularity with parents, certain problems persist which militate against obtaining a totally satisfactory diaper. First, it is necessary that the diapers be capable of receiving and absorbing sudden surges of urine while preventing leaking. At the same time, the diapers should provide a comfortable fit for the infant. Further, the diapers should be made in an economical manner to lower the cost to the consumer, since they are discarded after a single use.

SUMMARY OF THE INVENTION

A principal feature of the present invention is the provision of a disposable diaper of simplified construction which is contourable to the shape of an infant and which prevents leakage.

The disposable diaper of the present invention comprises, an absorbent pad assembly having a pair of waistline portions, a crotch portion intermediate the waistline portions, a fluid impervious backing sheet, a fluid pervious cover sheet, and an absorbent pad intermediate the backing and cover sheets. The pad assembly may have a plurality of longitudinally extending folds defining a pleated configuration of the diaper having a longitudinally extending central panel, and a pair of outermost panels overlying the central panel. The pad assembly also has a lateral fold of the pleated pad assembly in the crotch region. The diaper has means for securing a sufficient portion of the outermost panels together in the lateral fold to maintain the pad assembly in its laterally folded configuration.

Thus, a feature of the invention is that the diaper assumes a contoured configuration responsive to longitudinal expansion of the central panel.

Another feature of the invention is that the longitudinally expanded diaper forms a pocket in the crotch region of the diaper to receive and dissipate sudden surges of urine, as well as collect solid waste matter.

A further feature of the invention is that in an embodiment of the diaper the absorbent pad includes cut-out portions in the lateral fold, thus reducing the cost of the diaper to the consumer and reducing bulk of the diaper in the crotch region.

Yet another feature of the invention is the provision of a disposable diaper having an absorbent pad separated in the crotch region of the diaper and defining a laterally extending area of reduced thickness to facilitate folding of the diaper in the laterally extending area.

Further features will become more fully apparent in the following description of the embodiments of this invention and from the appended claims.

DESCRIPTION OF THE DRAWINGS

In the drawings:

FIG. 1 is a front plan view of a diaper of the present invention prior to folding into a pleated configuration;

FIG. 2 is a perspective view of the diaper of FIG. 1 as folded into a longitudinally pleated configuration, and having a lateral pleat partially formed in the crotch region of the diaper;

FIG. 3 is a fragmentary front plan view of the laterally pleated diaper of FIG. 2;

FIG. 4 is a fragmentary elevational view of the diaper of FIG. 3;

FIG. 5 is a perspective view illustrating the diaper of FIGS. 3 and 4 as unfolded during placement on an infant;

FIG. 6 is a perspective view of another embodiment of the diaper of the present invention;

FIG. 7 is a perspective view of another embodiment of the diaper of the present invention; and FIG. 8 is a fragmentary elevational view of another embodiment of the diaper of the present invention.

DESCRIPTION OF THE PREFERRED EMBODIMENTS

Referring now to FIGS. 1 and 2, there is shown a disposable diaper generally designated 20 having an absorbent pad assembly 22. The pad assembly has a pair of side edges 24a and 24b, a pair of end edges 26a and b connecting the side edges 24a and b, a fluid impervious backing sheet 28 defining a back surface 30 of the diaper, and a fluid pervious cover sheet 32 defining a substantial portion of a front surface 34 of the pad assembly. The pad assembly has a pair of waistline portions 38a and 38b and a crotch portion 40 intermediate the waistline portions. The diaper may have a pair of conventional tape strips 41a and 41b adjacent the waistline portion 38a for securing the diaper about an infant.

The pad assembly has a pair of spaced absorbent pads 36a and 36b intermediate the backing and cover sheets 28 and 32, with the separated pads defining a laterally extending area 42 of reduced thickness in the crotch region 40 of the diaper. The pads 36a and b are preferably spaced approximately an equal distance, such as ½ inch (1.27 cms.) to 2 inches (5.08 cms.), from the longitudinal mid-point of the diaper.

The diaper of FIG. 1 is folded along a plurality of longitudinally extending fold lines 44a, 44b, 44c, and 44d into a box-pleat configuration, as shown in FIG. 2. The fold lines 44a, b, c, and d define a longitudinally extending central panel 46, a pair of first panels 48a and 48b extending from and overlying the front surface 34 of the central panel 46, and a pair of outermost panels 50a and 50b extending from and overlying the first panels 48a and b.

As illustrated in FIG. 2, the pad assembly 22 also has a lateral tuck 52 of the box-pleat pad assembly in the crotch region 40, with the tuck 52 having a lateral fold line 54 adjacent the longitudinal mid-point of the pad assembly, and first and second longitudinal sections 56a and 56b, respectively, extending from the lateral fold line 54 toward opposite waistline portions 38a and b of the pad assembly. As illustrated in FIGS. 2–4, the longitudinal sections 56a and b of the outermost pleats 50a and b in the lateral tuck 52 are secured together by suitable means 58, such as adhesive or heat sealing. The securing means 58 thus retains overlapped portions of the outermost panels 50a and b together in the area of reduced thickness 42 of the pad assembly, and retains a sufficient lateral portion of the outermost panels together to maintain the pad assembly in its laterally tucked or folded configuration. Preferably, the securing means 58 extends laterally across the outermost panels 50a and b, with a part of the securing means being located at inner portions of the outermost panels adjacent the first panels 48a and b. As best illustrated in FIGS. 3 and 4, the pads 36a and b may extend to adjacent the lateral tuck 52. As shown, the lateral tuck 52 depends from the longitudinal central portion of the pad assembly.

As illustrated in FIG. 5, when the diaper 20 is unfolded and the central panel 46 is longitudinally expanded during placement of the diaper, the pads 36a and b separate in the crotch region 40 of the diaper, and the pad assembly assumes a contoured configuration to provide an improved fit for the infant. Moreover, the lateral tuck of the expanded diaper forms a pocket to receive sudden surges of urine from the infant, after which the urine passes into absorbent pads 36a and b from the pocket. The pocket also receives and retains solid waste matter from the infant. It is apparent that the cut-out portion of the absorbent pad in the lateral tuck decreases the cost of the diaper to the consumer, since a reduced amount of absorbent material is required. Further, the area of reduced thickness in the lateral tuck reduces the bulk of the diaper in the crotch region, and provides a comfortable fit for the infant.

Another embodiment of the diaper of the present invention is illustrated in FIG. 6, in which like reference numerals designate like parts. In this embodiment, which is similar in most respects to the embodiment described in connection with FIGS. 1-5, a single absorbent pad 36 may extend through the lateral tuck 52 of the pad assembly 22. Securing means 58, such as adhesive, is utilized to retain the outermost panels 50a and b in the lateral tuck together, as previously described. The operation of the diaper of FIG. 6 is similar to that of the diaper described in connection with FIGS. 1-5 in forming a contoured configuration responsive to lateral expansion of the central panel 46, and in forming a pocket in the lateral tuck after longitudinal expansion of the diaper. Although the advantages associated with the lateral area of reduced thickness in the previous diaper are not present in the diaper of FIG. 6.

Another embodiment of the diaper of the present invention is illustrated in FIG. 8, in which like reference numerals designate like parts. In this embodiment, the lateral area of reduced thickness 42 of the longitudinally pleated pad assembly is folded into a lateral pleat 53 in the crotch region 40. The pleat has a pair of lower fold lines 55a and 55b and an upper fold line 55c defining a plurality of contiguous longitudinal sections 57a, 57b, 57c, and 57d. The longitudinal sections 57a, b, c, and d in the pleat 53 are retained together by suitable means 58', such as an adhesive line or spot 59a intermediate the sections 57a and b and an adhesive line or spot 59b intermediate the sections 57c and d, as shown, or a heat seal extending through the sections 57a, b, c, and d. The securing means 58' preferably retains a sufficient lateral portion of the outermost panels together in the pleat to maintain the pad assembly in its laterally pleated or folded configuration. The operation of the diaper of FIG. 8 is similar to that of the diaper described in connection with FIGS. 1-5 in forming a contoured configuration responsive to lateral expansion of the central panel, and in forming a pocket in the lateral pleat 53 after longitudinal expansion of the diaper.

Another embodiment of the diaper of the present invention is illustrated in FIG. 7, in which like reference numerals designate like parts. In this embodiment, the absorbent pads 36a and b may be slightly spaced from each other adjacent the longitudinal mid-point of the pad assembly forming a laterally extending area 42 of reduced thickness in the crotch region 40 of the diaper. The laterally extending area of reduced thickness facilitates folding of the diaper about a lateral fold line 62 in the area during manufacture of the diaper, since it is unnecessary to fold the pad assembly through the thickness of an absorbent pad, and a mulit-layer thickness of the pad in the case of a box-pleat diaper.

Thus, there has been described a diaper which assumes a contoured configuration responsive to longitudinal expansion of the diaper and provides an improved fit for an infant. Moreover, the expanded diaper of the present invention forms a pocket to receive solid and liquid waste from the infant without leakage. In a preferred embodiment of the diaper, the diaper has a reduced amount of absorbent material, thus reducing the cost of the diaper to the onsumer.

The foregoing detailed description is given for clearness of understanding only, and no unnecessary limitations should be understood therefrom, as modifications will be obvious to those skilled in the art.

What is claimed is:

1. A disposable diaper, comprising:
   an absorbent pad assembly having a pair of waistline portions, a crotch region intermediate the waistline portions, a fluid impervious backing sheet, a fluid pervious cover sheet, an absorbent pad intermediate the backing and cover sheets, a plurality of longitudinally extending folds defining a pleated configuration of the pad assembly having a longitudinally extending central panel, and a pair of outermost panels overlying the central panel, and lateral fold means of the pleated pad assembly in said crotch region; and
   means for securing a sufficient portion of the outermost panels together in said lateral fold means to maintain the pad assembly in its laterally folded configuration, whereby the diaper assumes a contoured configuration responsive to longitudinal expansion of the central panel.

2. The diaper of claim 1 wherein the securing means extends substantially laterally across the outermost panels.

3. The diaper of claim 1 wherein the longitudinally extending folds define a box-pleat configuration of the pad assembly having a pair of first panels extending from and overlying the central panel, and the outermost panels extending from and overlying the first panels.

4. The diaper of claim wherein said lateral fold means comprises a lateral tuck in the pad assembly.

5. The diaper of claim 4 wherein said lateral tuck includes a lateral fold line, and first and second longitudinal sections of the pad assembly extending from the lateral fold line toward opposite waistline portions of the pad assembly.

6. The diaper of claim 5 wherein the longitudinal length of each of the longitudinal sections is approximately ½ inch (1.27 cms.) to 2 inches (5.08 cms.).

7. The diaper of claim 5 wherein said lateral fold line is located adjacent the longitudinal mid-point of the pad assembly.

8. The diaper of claim 1 wherein said absorbent pad extends through a substantial portion of said lateral fold means.

9. The diaper of claim 1 wherein said absorbent pad includes cut-out portions in the outermost panels located in said lateral fold means.

10. The diaper of claim 1 wherein said absorbent pad includes a cut-out portion in said lateral fold means.

11. The diaper of claim 1 wherein at least a part of the securing means retains inner portions of the outermost panels together adjacent its inner edges.

12. The diaper of claim 1 wherein said lateral fold means comprises a lateral pleat in the pad assembly.

13. The diaper of claim 12 wherein said pleat has a pair of lower fold lines and an upper fold line defining a plurality of contiguous longitudinal sections in the pad assembly.

14. The diaper of claim 13 wherein the securing means retains said sections together.

15. A disposable diaper comprising, an absorbent pad assembly having a pair of side edges, a pair of waistline portions, a crotch portion intermediate the waistline portions, a fluid impervious backing sheet, a fluid pervious cover sheet, and a pair of absorbent pads intermediate the backing and cover sheets, said pads being separated in the crotch region of the diaper defining a laterally extending area of reduced thickness.

16. The diaper of claim 15 wherein the pad assembly is folded laterally in the area of reduced thickness, said area facilitating folding of the pad assembly.

17. The diaper of claim 15 including means for securing folded portions of the pad assembly in said area of reduced thickness.

18. The diaper of claim 15 wherein the pad assembly has a plurality of longitudinally extending folds defining a box-pleat configuration of the diaper having a longitudinally extending central panel, a pair of first panels extending from and overlying the central panel, and a pair of outermost panels extending from and overlying the first panels, and including means for securing overlapped portions of the outermost panels together in said area of reduced thickness.

19. The diaper of claim 18 wherein at least a part of the securing means retains inner portions of the outermost panels together adjacent the first panels.

20. The diaper of claim 18 wherein the securing means extends laterally across the outermost panels.

21. The diaper of claim 18 wherein said pads are spaced approximately the same distance from the longitudinal mid-point of the pad assembly, and said pad assembly is laterally tucked adjacent the longitudinal mid-point of the diaper to overlap said outermost panels.

22. The diaper of claim 18 wherein said pads are spaced approximately the same distance from the longitudinal mid-point of the pad assembly, and said pad assembly is laterally pleated adjacent the longitudinal mid-point of the diaper to overlap said outermost panels.

23. A disposable diaper comprising, an absorbent pad assembly having front and back waistline portions, a fluid impervious backing sheet, a crotch region intermediate the waistline portions, and securing means for retaining spaced areas of said backing sheet in a close relationship to define pocket means of said backing sheet in the crotch region depending from the pad assembly in the crotch region to receive body exudate from an infant.

* * * * *